United States Patent [19]

Termin et al.

[11] Patent Number: 5,071,407
[45] Date of Patent: Dec. 10, 1991

[54] RADIALLY EXPANDABLE FIXATION MEMBER

[75] Inventors: Paul L. Termin, St. Paul, Minn.; Christopher H. Porter, Woodenville, Wash.

[73] Assignee: Schneider (U.S.A.) Inc., Minneapolis, Minn.

[21] Appl. No.: 508,854

[22] Filed: Apr. 12, 1990

[51] Int. Cl.$^5$ .............................................. A61M 29/00
[52] U.S. Cl. .................................... 604/104; 604/174; 606/194
[58] Field of Search ............... 623/1, 11, 12; 128/642, 128/784, 785, 786; 604/96, 104–109, 174, 175; 606/159, 180, 191, 194

[56] References Cited

U.S. PATENT DOCUMENTS

| | | | |
|---|---|---|---|
| 3,868,956 | 3/1975 | Alfidi et al. | |
| 4,553,545 | 11/1985 | Maass et al. | 604/104 |
| 4,572,186 | 2/1986 | Gould et al. | 604/104 |
| 4,649,922 | 3/1987 | Wiktor | 623/1 |
| 4,655,771 | 4/1987 | Wallsten | 623/1 |
| 4,681,110 | 7/1987 | Wiktor | |
| 4,699,611 | 10/1987 | Bowden | 604/105 |
| 4,723,549 | 2/1988 | Wholey et al. | 606/194 |
| 4,732,152 | 3/1988 | Wallsten et al. | 623/1 |
| 4,733,665 | 3/1988 | Palmaz | 623/1 |
| 4,793,348 | 12/1988 | Palmaz | |
| 4,800,882 | 1/1989 | Gianturco | 623/13 |
| 4,830,003 | 5/1989 | Wolff et al. | 623/1 |
| 4,848,343 | 7/1989 | Wallsten et al. | 604/271 |
| 4,856,516 | 8/1989 | Hillstead | 604/96 |
| 4,886,062 | 12/1989 | Wiktor | 623/1 |
| 4,921,484 | 5/1990 | Hillstead | 604/104 |

OTHER PUBLICATIONS

"Transluminally-Plated Coilspring Endarterial Tube Grafts", Charles T. Dotter, M.D., pp. 329–332, *Investigative Radiology*, Sep.–Oct. 1969, vol. 4.

Technical Developments and Instrumentation, "Transluminal Expandable Nitinol Coil Stent Grafting: Preliminary Report", Dotter et al., pp. 259–260, *Radiology* 147, Apr. 1983.

"Astherosclerotic Rabbit Aortas: Expandable Instruminal Grafting", *Radiology*, 1986 (Sep.), pp. 723–726, Palmaz et al.

*Interventional Radiology*, "Self-Expanding Metallic Stents for Small Vessels: an Experimental Evaluation", Duprat et al., pp. 469–472, vol. 162, Feb. 1987, *Radiology*.

"Self-Expanding Endovascular Prosthesis: An Experimental Study", *Radiology* 1987, (Sep.), pp. 709–714, Rousseau et al.

"When Hope is all in Vein", *Sweden Now*, Mar. 1988.

"The Temporary Stent Catheter: A Non Operative Treatment for Acute Occlusion During Coronary--Trigioplasty", Gaspard et al., *JACC*, vol. 15, No. 2, Feb. 1990, pp. 1A; 118A.

*Primary Examiner*—Randy Citrin Shay
*Attorney, Agent, or Firm*—Haugen and Nikolai

[57] ABSTRACT

An open weave fixation device is secured to a distal end region of a catheter or other diagnostic or treatment device, for either temporarily or permanently fixing the device within a body cavity. In one approach, the fixation element is constructed of braided, helically wound filaments of resilient stainless steel. A sheath surrounds the catheter and fixation element to elastically deform the element into a reduced radius configuration to facilitate insertion and deployment. With the fixation element positioned as desired, the sheath is withdrawn to permit the fixation element to self-expand against body tissue, thus to secure the fixation element and catheter. In an alternative arrangement, a dilatation balloon surrounds a catheter near its distal end, and in turn is surrounded by a plastically deformable fixation element. Following desired positioning, the balloon is dilated to permanently deform the fixation element into contact with body tissue. In either case, the fixation element can be mounted at its distal end, its proximal end or medially, depending upon the particular treatment and the expected duration of fixation. Another approach employs a recovery metal in the fixation element.

21 Claims, 2 Drawing Sheets

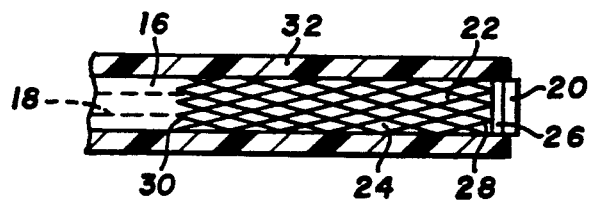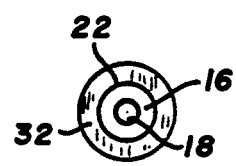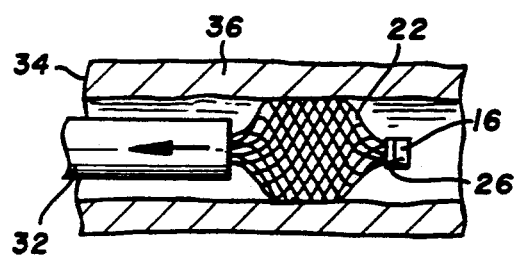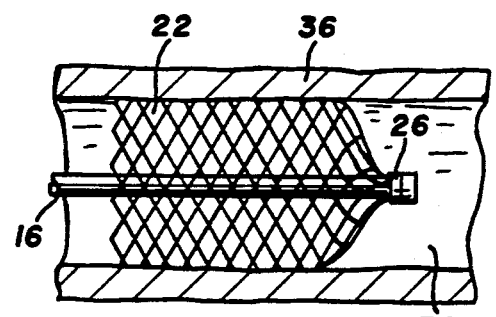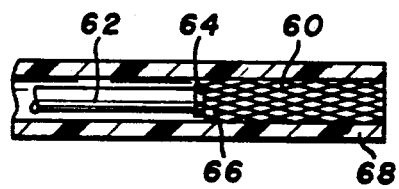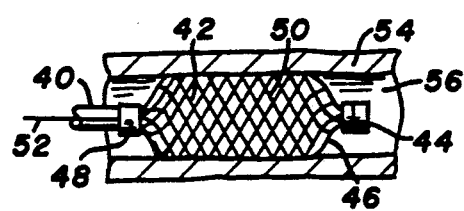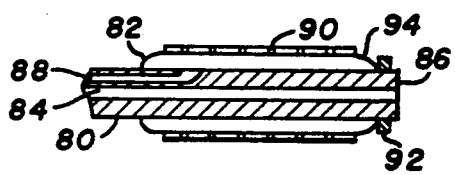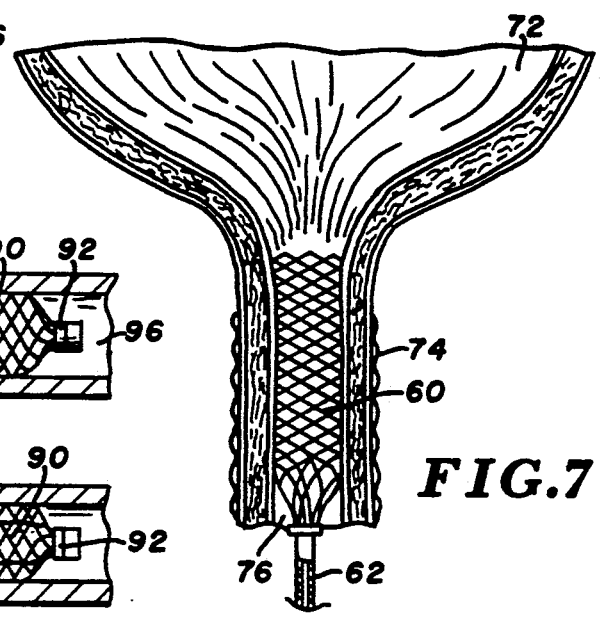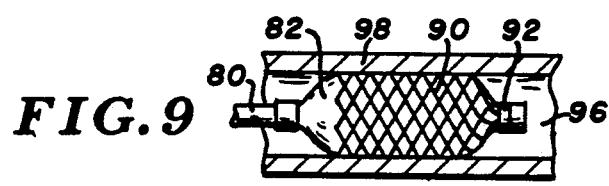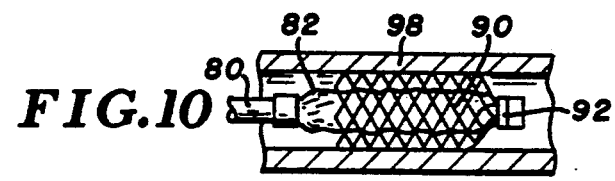

RADIALLY EXPANDABLE FIXATION MEMBER

BACKGROUND OF THE INVENTION

The present invention relates to body implantable treatment devices, and more particularly to apparatus for securing such devices at predetermined locations within the body.

A wide variety of patient treatment and diagnostic procedures involve the use of devices inserted into the body of the patient, with some of these devices being either temporarily or permanently implanted. Among the permanently implanted devices are prostheses or grafts for transluminal implantation, for example as disclosed in U.S. Pat. No. 4,655,771 (Wallsten). The prosthesis described in Wallsten is a flexible tubular braided structure formed of helically wound thread elements. Gripping members at opposite ends of the prosthesis initially secure it to a catheter, with the proximal gripping member being movable distally to give the tube the shape of a balloon. In deployment, the gripping members and catheter are removed, leaving the tube to assume a cylindrical shape.

Another device, disclosed in U.S. Pat. No. 4,793,348 (Palmaz), is a balloon expandable vena cava filter. The filter has an open weave structure, and can be provided with hooks at terminal ends of the strands forming the weave for securing the filter to body tissue. The filter is said to prevent lower extremity venous clots from migrating into the pulmonary circulatory system.

U.S. Pat. No. 4,699,611 (Bowden) is directed to a biliary stent which is tubular and provided with axially running slits which form parallel strips. The strips become flowered to form a Mallecot tip when relaxed, but collapse when the stent is maintained in tension. Other permanently implanted devices include electrically conducted intravascular leads for cardiac pacing or defibrillation devices, and catheters for delivering drugs or sensing temperatures, flow rates or other conditions within the body. Catheters frequently are used temporarily, with no intention of even temporary implantation, for example in percutaneous transluminal catheter angioplasty (PTCA) procedures.

Pacing leads typically are sufficiently flexible and small in diameter for intravenous introduction to the cardiac cavity, whereupon an electrode at the distal end of the lead is implanted into the endocardium to secure the lead. For this purpose, helical coils, barbs and other anchoring elements are provided, usually as part of the electrode. The anchoring element must be sufficiently sharp to penetrate the endocardium and secure the electrode against becoming detached, for example due to contractions of the myocardium. A problem with such anchoring elements is that they can become entangled in the vein, heart valve or other tissue encountered during intravenous insertion. Flexible outwardly extended tines, usually constructed of plastic, afford a safer intravenous insertion of the lead, yet do not provide the positive anchoring of helical coils or the like.

An example of a temporarily implanted treatment device is the Foley catheter, designed to overcome an obstruction in the urinary tract, or a constriction due to collapse of the sphincter during and after surgery. Typically, a catheter is fixed in the urinary tract near the opening into the bladder by means of a dilated balloon. One disadvantage of this approach, however, is due to the surface area where the fixation balloon and urinary tract are contiguous. This area retains moisture which promotes the growth of harmful bacteria and can lead to infection, spreading throughout the urinary tract.

Thus, there remains a need for a positive fixation device which is reliable, convenient to deploy and minimizes the chance of infection.

Therefore, it is an object of the present invention to provide a fixation means particularly well suited for securing implantable devices within body cavities. Another object is to provide a fixation means adaptable for either temporary or permanent placement within the body.

Yet another object is to provide a fixation means for catheters and other diagnostic and treatment devices to provide a positive initial securement and improved long-term fixation by promoting fibrosis, while reducing the probability of infecting tissue in the region of fixation.

SUMMARY OF THE INVENTION

To achieve these and other objects, there is provided a body implantable apparatus. The apparatus includes an elongate bodily insertable device having a proximal end region and a distal end region, and a nominal diameter which preferably is sufficiently small to facilitate intravenous insertion. A tubular fixation element is fastened to the distal end region of the device. The fixation element is formable into a delivery configuration in which the fixation element has a diameter approximately equal to the nominal diameter, and is radially expandable to a fixation configuration in which the fixation element diameter is substantially greater than the nominal diameter. A deployment means is operatively associated with the device for delivering the fixation element in the delivery configuration as the device is bodily inserted to selectively position the fixation element at a predetermined location within a body cavity. The deployment means further causes a radial expansion of the fixation element into a surface engagement with a tissue wall segment defining the cavity at the predetermined location. This secures the fixation element to the wall segment and thus substantially fixes the distal end region of the device within the body cavity.

In one preferred form, the fixation element is flexible and, when in a relaxed state, has a diameter substantially greater than the nominal diameter. The deployment means in this case is a sheath surrounding the fixation element and device at least along the distal end region. The sheath is movable relative to the device, in particular retractable from around the fixation element to allow the fixation element to self-expand radially under its restoring force. The preferred flexible fixation element is formed of a plurality of helically wound or braided strands in an open weave cylindrical configuration.

Alternatively, the fixation element can be plastically deformable, and delivered to the fixation site in the reduced radial or delivery configuration. When the device is a pliable catheter, a suitable deployment means includes a pliable balloon surrounding the catheter at the distal end region, and in turn surrounded by the fixation element. A balloon inflation lumen is formed in the catheter and open to the interior of the balloon, for dilatation of the balloon responsive to supplying a fluid under pressure through the balloon inflation lumen. As the balloon expands, it plastically deforms the fixation element to enlarge its radius. Again, the fixation element is preferably an open mesh construction, and may or may not shorten in its axial length as it expands radially, depending on the design. Yet another alternative is a helical coil element constructed of a recovery metal, expanding radially when heated after deployment.

Whether plastically or elastically deformable, the fixation elements may be attached to their associated catheters or other devices in a manner corresponding to the intended purpose. For example, the fixation element may be attached to the device only at its distal end to enable a permanent implantation particularly resistant to proximal movement of the device. Or, the fixation element may be attached only at its proximal end, for an arrangement which provides fixation, yet enables subsequent proximal removal of the device and fixation element. Yet another approach involves integral securement of the distal end of the fixation element to the device, in combination with a slidable mounting of the proximal end. This results in the fixation element assuming the shape of a typical catheter dilatation balloon, with movement of the slidable end to manipulate the fixation element in much the same manner as inflation and evacuation manipulate the shape of the catheter balloon.

The preferred material for the helical strands of the fixation element is a biocompatible and corrosion resistant stainless steel, although other body compatible metals as well as plastics may be employed. In any event, the fixation element is preferably constructed to allow for expansion to a fixation radius two times the deployment radius. In a particularly referred approach, an elastically deformable open weave braided cylinder is compressed to a diameter of about seven French (2⅓ mm), and is capable of expanding to a diameter of approximately 10 mm. The compressed diameter is small enough to enable convenient intravascular insertion of a catheter or other device to be fixed, while the potential radial expansion is more than sufficient for engaging the walls of a blood vessel or other body cavity short of complete expansion, with sufficient restoring force remaining for fixing the device. Migration of the device is effectively resisted by the braided structure. In particular, when the braided fixation element is secured medially to the device being fixated, migration of the device in either axial direction tends to axially shorten a portion of the fixation element in the direction of migration, thus to radially enlarge that portion and increase resistance to further migration. Typically the tissue permits some embedding of the fixation element, which further enhances the ability to secure the device. The open weave or open mesh construction minimizes fluid entrapment and thus does not promote infection at the fixation site. Further, this construction promotes fibrosis about the strands of the fixation member, for improved chronic fixation in connection with permanently implanted devices.

IN THE DRAWINGS

For a further understanding of the above and other features and advantages, reference is made to the following detailed description and to the drawings, in which:

FIG. 1 is a side sectional view of a catheter and accompanying fixation element constructed in accordance with the present invention;

FIG. 2 is an end view of the catheter and fixation element of FIG. 1;

FIG. 3 is a side view illustrating deployment of the catheter of FIG. 1;

FIG. 4 is a side view showing the catheter after deployment;

FIG. 5 is a side view of an alternative embodiment catheter when deployed;

FIG. 6 is a side sectional view of another alternative embodiment catheter and fixation element constructed in accordance with the present invention;

FIG. 7 is a diagrammatical view illustrating the catheter of FIG. 6 when deployed;

FIG. 8 is a side sectional view of yet another alternative embodiment catheter and fixation element constructed in accordance with the present invention;

FIG. 9 is a side elevation illustrating the deployment of the catheter of FIG. 8;

FIG. 10 is a side view illustrating the fixation of the catheter of FIG. 8 following deployment;

DETAILED DESCRIPTION OF THE PREFERRED EMBODIMENTS

Figure 11:
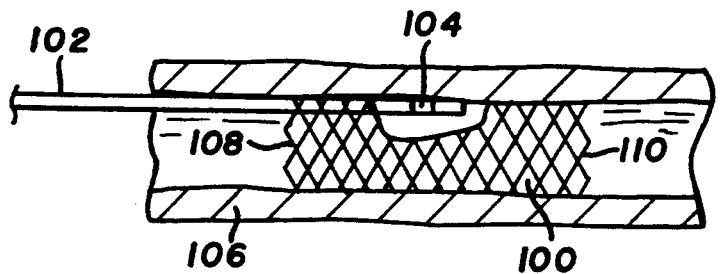
FIG. 11 is a side view of a further embodiment catheter and fixation element when deployed.

Turning now to the drawings, there is shown in FIGS. 1 and 2 the distal end region of a catheter 16. Catheter 16 is elongate, tubular and pliable, and preferably is constructed of silicone rubber, polyethylene or other suitable elastomeric material. A central lumen 18 is open to the distal tip 20 of the catheter, and runs the length of the catheter to permit delivery of a drug, in liquid form, to the catheter distal tip from a supply at the proximal end of the catheter (not shown). Alternatively, an electrically conductive coil may be contained within the lumen, for transmitting electrical pulses between the proximal end of the catheter and an electrically conductive lead at or proximately the distal tip, in which case the catheter is dielectric. The lead and coil are neither illustrated nor further discussed herein, as they are well known and not particularly germane to the present invention.

A tubular fixation element 22 surrounds catheter 16 at the distal end region 24. Fixation element 22 is of open weave construction, preferably formed of braided multiple strands or filaments of resilient and body compatible stainless steel. Suitable alternative materials for the fixation element include other body compatible metals, as well as elastically deformable and body compatible plastics, for example polyethylene, polyurethane, polypropylene or nylon.

A stainless steel ring 26 is secured to the distal end 28 of fixation element 22 and fixedly secures the fixation element to catheter 16. The proximal end 30 of the fixation element is not integrally fastened to the catheter, and is free to move axially relative to the catheter as fixation element 22 radially expands.

The fixation element is self-expanding in the sense that when it is not subject to external stress, it has a diameter much larger than that illustrated in FIGS. 1 and 2. In these figures, the fixation element is elastically deformed, maintained in a radially reduced configuration by a pliable sheath 32 surrounding catheter 16 and the fixation element. Sheath 32 preferably is constructed of silicone rubber or other suitable biocompatible material, and surrounds the catheter and fixation element at least along the distal end region. If desired, sheath 32 can run the length of catheter 16. Sheath 32 preferably is thin to facilitate intravascular insertion of the catheter and sheath, yet of a sufficient thickness to maintain fixation element 22 in the reduced radius configuration against the restoring force of the fixation element strands. The outside diameter of the assembly including the catheter, fixation element and sheath can be in the range of from 5 to 9 French, i.e., 1.7 to 3 millimeters.

Fixation element 22 is particularly well suited for anchoring catheter 16 within a body cavity, for example a blood vessel 34 having a blood vessel wall including a tissue wall segment 36. The assembly is deployed initially with fixation element 22 in the reduced radius configuration, which facilitates movement of the assembly through blood vessel 34 until the distal region of catheter 16 reaches a predetermined location or position along the blood vessel. Radiopaque markers can be provided on catheter 16 in a known manner to assist in positioning. Once the desired position of the catheter is confirmed, sheath 32 is moved proximally with respect to catheter 16. Due to ring 26, such movement also withdraws the sheath from fixation element 22, permitting the fixation element to self-expand into an engagement with tissue wall segment 36.

As seen from FIG. 4, the sheath 32 removed the fixation member is radially expanded over the majority of its length including proximal end 30, such that its diameter is substantially greater than the diameter of catheter 16. While not fully expanded to a relaxed state, the fixation member is sufficiently expanded to cause a limited radial expansion of the wall of blood vessel 34, to an equilibrium of the fixation element restoring force and a counteracting restoring force in tissue wall segment 36. As a result, fixation element 22 is firmly secured with respect to the tissue wall segment, and thus substantially integrally secures catheter 16 within the blood vessel.

A salient feature of the present invention is the open weave construction of fixation element 22. So constructed, the fixation element secures catheter 16 with respect to tissue wall segment 36 without interfering with passage of blood through the blood vessel. Contact between the fixation element and tissue wall segment is along the individual strands or filaments, which avoids altogether any large areas of surface contact between the fixation element and blood vessel wall. Finally, the open weave construction promotes fibrotic growth near the filaments and in spaces between filaments, a long term process which further improves the mounting of the catheter. A balloon mounted at the catheter distal end could of course secure the catheter, but by contrast would block the flow of blood, contact the blood vessel wall over a relatively large contiguous area and fail to promote or encourage fibrosis.

FIG. 5 illustrates an alternative embodiment assembly including a catheter 40 which can be similar in construction to catheter 16, a fixation element 42, a ring 44 for integrally securing the distal end 46 of the fixation member to catheter 40, and a proximal ring 48 fixed to the proximal end of the fixation member and mounted slidably on catheter 40. Fixation element 42 is constructed of strands or filaments 50 of a resilient stainless steel (or another of the suitable materials mentioned above, and like fixation element 22, is elastically deformable to a delivery configuration in which its diameter is substantially equal to but slightly larger than the diameter of the catheter.

A fine wire 52 runs the length of the catheter so that it may be manipulated at the proximal end of the catheter. Wire 52 is used to pull proximal ring 48 leftward as viewed in FIG. 5 against the restoring force of the fixation element, to axially elongate the fixation element and maintain it in the delivery configuration. Once the distal end region of catheter 40 is aligned with a tissue wall segment 54 of a blood vessel 56, wire 52 is released to allow the fixation member to radially self-expand until it contacts the tissue wall segment, which of course causes proximal ring 48 to slide on catheter 40, rightwardly to the position shown in FIG. 5. Thus fixation element 42 assumes the shape of a dilated catheter balloon in order to secure the catheter, and may be utilized for either temporary or permanent fixation.

FIG. 6 illustrates another embodiment of the assembly with a fixation element 60 of similar construction to the previously described fixation elements. Fixation element 60 is integrally secured to the distal end region of an elongate catheter 62, by a ring 64 integral with the proximal end 66 of the fixation element. A sheath 68 extends well beyond the distal tip of the catheter to surround the fixation element and thus maintain it in a reduced radius or delivery configuration. In other respects, sheath 68 is similar to sheath 32 of the first embodiment, in that sheath 68 is movable with respect to catheter 62 and fixation element 60. Thus the sheath can be withdrawn, to the left as viewed in FIG. 6, to allow the fixation element to radially expand.

As seen in FIG. 7, catheter 62 can be employed as an alternative to a catheter within the urinary tract. More particularly, fixation element 60 is positioned near the opening of bladder 72 as a drain catheter within the urethra 76. As noted above, this type of catheter is particularly useful to overcome a blockage in the urinary tract, or used following surgery in the event that the internal sphincter and external sphincter have collapsed. Typically a bag, not shown, receives fluid at the proximal end of drain catheter 62.

Fixation element 60, with its proximal end 66 secured to the distal end of the drain catheter, is particularly well suited for use with this type of catheter. First, due to the open weave construction, there are no large areas where the fixation element and walls of the urinary tract are contiguous. This avoids the trapping of fluids and risk of infection associated with the conventional balloon employed to mount such catheters. Due to the proximal end mounting of fixation element 60, sheath 68 can be advanced over the catheter, upwardly as viewed in FIG. 7, to elastically deform the fixation element into its delivery configuration once again. This facilitates removal of drain catheter 62 from the urinary tract, a useful feature in that the catheter is intended for only temporary fixation. Fixation element 60 can advantageously extend nearly the entire length of the urethra, for a secure albeit temporary fixation and, more importantly, an infection resistant pathway.

A specific approach found satisfactory in connection with this catheter utilizes 0.120 millimeter diameter spring steel wire to form fixation element 60. When constrained by sheath 68, the fixation element has a diameter of approximately 7 French (2⅓ millimeters) and a length of about 30 millimeters. The normal diameter of the fixation element, when it is free of any constraint, is about 10 millimeters, which of course is greater than its diameter when deployed as illustrated in FIG. 7.

While sheath 68 is shown as a dielectric tubular member for convenience in its illustration, alternatives can be employed, for example a rigid tubular member of sufficiently short length. A particularly preferred approach involves a rolling membrane of extruded polyurethane, folded over upon itself at the distal end of the assembly. The radially outward layer of the sheath is moved proximally, which withdraws the fold to expose and release the fixation element.

As mentioned above, the proximal end mounting of fixation element 60 facilitates removal of drain catheter 62 when it no longer is needed. As compared to the distal end attachment of the fixation element illustrated in FIGS. 1-4, proximal attachment offers less resistance to downward migration as viewed in FIG. 7. To provide increased resistance to downward migration and yet facilitate eventual removal of catheter 62, fixation element 60 can be constructed of a resorbable material as employed in sutures, for example PGA (polyglycolic acid). Consequently the element provides positive fixation against downward migration. After a predetermined period of time based on the material selected and diameter of the braided strands, bodily fluids break down and assimilate the fixation element to permit removal of the catheter.

FIG. 8 illustrates yet another embodiment of the invention in which a distal end region of a balloon catheter 80 is surrounded by a balloon 82. Catheter 80 includes a central lumen 84 running from a distal tip 86 of the catheter to the proximal end of the catheter. Further, a balloon inflation lumen 88 runs from the proximal end of the catheter to the distal end region, and is open to the interior of catheter balloon 82. Balloon 82 is dilated when desired, by supplying a fluid under pressure to the balloon through balloon inflation lumen 88.

In FIG. 8, balloon 82 is shown in the deflated or evacuated condition, and is surrounded by a fixation element 90, having an open weave construction like previously discussed fixation elements. Fixation element 90 differs, however, in that it is substantially inelastic, constructed of a plastically deformable material, e.g. tantalum, gold, certain stainless steels and plastics. Thus, when in the delivery configuration, this fixation element does not have a restoring force. A ring 92, on the distal end 94 of fixation member 90, secures the fixation element to the distal end of catheter 80.

FIGS. 9 and 10 show the fixation of balloon catheter 80 within a blood vessel 96 along a tissue wall segment 98 of the vessel. The catheter is inserted and positioned at a selected location along the blood vessel, with fixation element 90 in the delivery configuration. Once the catheter distal end region is properly aligned, balloon 82 is dilated by supplying fluid to the balloon, through balloon inflation lumen 88. As the balloon expands, it plastically deforms fixation element 90 to enlarge the radius of the fixation element except for the distal end portion near ring 92. To ensure proper fixation of the catheter, balloon 82 is dilated sufficiently to expand the fixation member into tissue wall segment 98 to at least slightly elastically deform the tissue wall segment.

Once the fixation member has been satisfactorily expanded, the inflation fluid is evacuated from the balloon and accordingly becomes flat once again. As illustrated in FIG. 10, the plastically deformed fixation element retains its expanded shape, thus to secure the catheter with respect to tissue wall segment 98. This embodiment, of course, is appropriate for situations requiring permanent or at least long term fixation of the catheter. While plastically deformable rather than resilient, fixation element 90 nonetheless exhibits the advantages discussed above in connection with the resilient fixation elements, including the absence of interference with passage of blood or other fluids, avoiding large surface contact areas between the fixation member and body tissue, and promoting fibrosis.

FIG. 11 illustrates a further alternative embodiment assembly with a fixation element 100 similar in construction to fixation elements 22, 42 and 60, secured to the distal end region of a catheter 102 by a ring 104 surrounding the catheter. A portion of fixation element 100 is removed to more clearly illustrate the ring. The fixation element is mounted medially rather than at its proximal or distal end, and further is attached to the ring circumferentially rather than being concentric with the catheter. As a result, when expanded after deployment as illustrated in FIG. 11, fixation element 100 positions the distal portion of the catheter adjacent a tissue wall segment 106 of a blood vessel, rather than near the center, thus to reduce disruption of or interference with passage of blood through the vessel. Due to the medial securing of the fixation element, a proximal end 108 and distal end 110 of the element are free of ring 104, or any other means securing the fixation element and catheter. This structure is particularly well suited to resist axial migration of the catheter, i.e. either to the left or right as viewed in the figure. Rightward migration, for example, tends to axially compress fixation element 100 in the region between ring 104 and distal end 110, which radially expands that portion of the fixation element to increase resistance to further migration. Likewise, any catheter migration to the left tends to radially expand that portion of the fixation element between the ring and proximal end 108. This arrangement of course contemplates permanent fixation of catheter 102, unless the fixation element is constructed of a resorbable material.

Figure 12:
FIG. 12 is a side sectional view of yet another embodiment fixation element and surrounding sheath.
Figure 13:
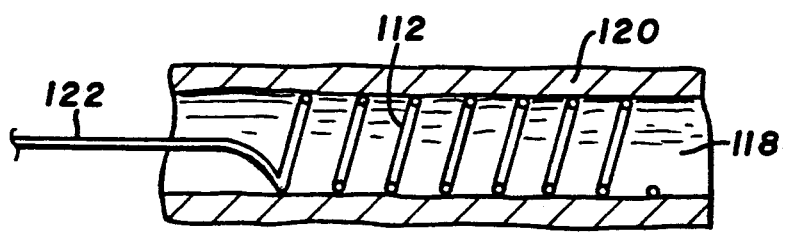
FIG. 13 is a side view of the fixation element of FIG. 12 when deployed.
Figure 14:
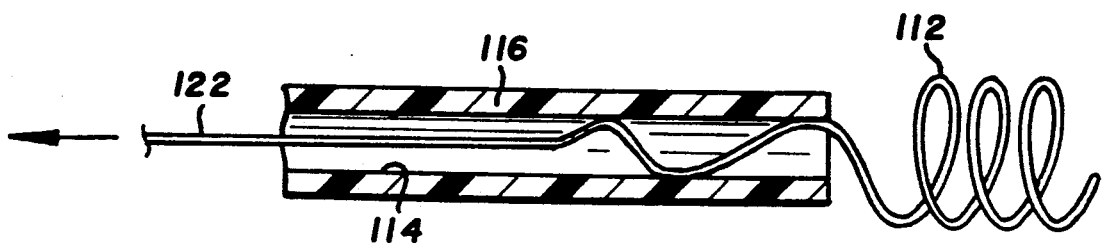
FIG. 14 is a side elevation illustrating the withdrawal of the fixation element of FIGS. 12 and 13.

FIGS. 12-14 illustrate a flexible fixation element 112 constructed of a recovery metal, e.g. an alloy of titanium and nickel as disclosed in U.S. Pat. No. 3,868,956 (Alfidi et al). Fixation element 112 is initially set in the configuration of a coil or helix of a specified pitch, then plastically deformed while cool into a substantially straight line configuration as shown in FIG. 12, where the fixation element is contained within a lumen 114 of a sheath 116.

Following deployment and positioning within a blood vessel 118, fixation element 112 is heated sufficiently to cause the element to return to the helical configuration whereby it expands to engage a tissue wall segment 120 of the blood vessel as shown in FIG. 13. In this instance, the device fixed within the blood vessel is a retrieval filament 122 shown as a substantially linear continuation of a single strand coiled at its distal end to form the fixation element. Alternatively, the filament can be constructed of biocompatible plastic or other material different from the material of the fixation element, and secured to the proximal end of the fixation element.

This assembly is suited for acute fixation following angioplasty, where localized fissuring of the intima can form a flap or piece of tissue that constricts or blocks the vessel. Fixation element 112, in the expanded or coil configuration shown in FIG. 13, presses the flap of tissue against wall segment 120, causing tissue to heal in a manner which permanently secures the flap against the remainder of the tissue wall segment. While a recovery metal is preferred, it is to be appreciated that fixation element 112 can, alternatively, be constructed of a flexible material for self-expansion when deployed.

When removal of fixation element 112 is desired, the proximal end of retrieval filament 122 is threaded into lumen 114 at the distal end of sheath 116, and the sheath is advanced distally over the filament until it reaches the proximal end of fixation element 102. At this point, the proximal end of filament 122 should extend proximally beyond the proximal end of sheath 116 enabling the filament to be grasped at the proximal end and moved proximally relative to the sheath, elastically deforming fixation element 112 as illustrated in FIG. 14 until the entire fixation element is contained within lumen 114. Then, the sheath device and fixation element are withdrawn from the blood vessel with minimal risk of damage to the vessel wall.

Thus, in accordance with the present invention, fixation of catheters and other treatment or diagnostic devices is accomplished without the moisture entrapment problems associated with dilatation balloons. Permanent fixation is achieved without the need for tissue penetrating coils or other sharp members which present the risk of damage to tissue during insertion and deployment. Finally, a fixation element in accordance with the present invention may be fixed to its associated device in a manner to assure a permanent fixation, or to enable removal if only temporary fixation is appropriate.

What is claimed is:

1. An apparatus for fixation in a body cavity, including:
   an elongate bodily insertable device having a proximal end region and a distal end region;
   a flexible tubular fixation element and a fastening means for securing the fixation element to a selected region of said device, said fixation element being formable into a delivery configuration in which the fixation element has a delivery diameter and radially expandable to a fixation configuration in which the fixation element diameter is substantially greater than the delivery diameter, said fixation element when in a relaxed state having a diameter substantially greater than said delivery diameter; and
   a deployment means operatively associated with said device for delivering said fixation element in said delivery configuration as said device is bodily inserted to selectively position said fixation element at a predetermined location within a body cavity, the deployment means including a restraining means for elastically deforming the fixation element into the delivery configuration and maintaining the fixation element in the delivery configuration against a restoring force, under which the fixation element tends to radially expand and controllable to allow radial expansion of said fixation element into a surface engagement with a tissue wall segment defining said cavity at said predetermined location, to secure the fixation element to said wall segment and thus substantially fix said selected region within said body cavity.

2. The apparatus of claim 1 wherein:
   said selected region of said device is said distal end region.

3. The apparatus of claim 2 wherein:
   said tubular fixation element is fastened concentrically on the distal end region of the device.

4. The apparatus of claim 3 wherein:
   said restraining means comprises a sheath surrounding said fixation element and said device at least in the area of said distal end region, said sheath being movable relative to said device to allow removal of the sheath from around the fixation element, thus to allow the fixation element to self-expand radially under said restoring force.

5. The apparatus of claim 4 wherein:
   said fixation element is an open weave tubular member constructed of helical, braided strands of a biocompatible material.

6. The apparatus of claim 5 wherein:
   said biocompatible material is stainless steel.

7. The apparatus of claim 5 wherein:
   said biocompatible material is a plastic.

8. The apparatus of claim 4 wherein:
   said sheath is pliable.

9. The apparatus of claim 4 wherein:
   said fixation element includes a plurality of helically wound strands forming an open weave cylinder.

10. The apparatus of claim 9 wherein:
    said fastening means comprises a ring integrally securing said fixation element to said distal end region of the device.

11. The apparatus of claim 10 wherein:
    said ring secures the proximal end of said fixation element to said device.

12. The apparatus of claim 10 wherein:
    said ring secures the distal end of said fixation element to said device.

13. The apparatus of claim 12 further including:
    a means for fastening the proximal end of said fixation element slidably relative to said device.

14. The apparatus of claim 10 wherein:
    said ring secures a medial portion of said fixation element to the device.

15. A process for deploying and fixing a body implantable device, including the steps of:
    securing a tubular fixation element to a distal end region of an elongate body insertable device;
    positioning a restraining means around the fixation element to maintain the fixation element in a delivery configuration against a restoring force;
    bodily inserting the device and fixation element and delivering the device and fixation element to a predetermined location within a selected body cavity, while maintaining the tubular fixation element in the delivery configuration in which the fixation element has a delivery diameter;
    with said fixation element at said predetermined location, removing the restraining means sufficiently to allow the fixation element to radially self-expand into a surface engagement with a tissue wall segment defining the cavity at the predetermined location, to secure the fixation element to the wall segment and substantially fix the distal end region within the body cavity.

16. An apparatus for fixation in a body cavity, including:
    an elongate bodily insertable device having a proximal end region and a distal end region;
    a flexible tubular fixation element and a fastening means for securing a distal end of the fixation element to a selected region of the device, said fixation element being formable into a delivery configuration in which the fixation element has a delivery diameter, and radially expandable to a fixation configuration in which the fixation element over the majority of its length has a fixation diameter substantially greater than the delivery diameter, said fixation element when in a relaxed state having a diameter greater than the fixation diameter; and a deployment means operatively associated with said device for delivering the fixation element in the delivery configuration as the device is bodily inserted to selectively position the fixation element at a predetermined location within a body cavity, said deployment means including a restraining means for elastically deforming the fixation element into the delivery configuration and maintaining the fixation element in the delivery configuration against a restoring force under which the fixation element tends to radially expand, said restraining means controllable to allow radial expansion of said fixation element over the majority of its length including a proximal end thereof, into surface engagement with a tissue wall segment defining said cavity at said predetermined location, to secure the fixation element to the wall segment and thus substantially fix said selected region within said body cavity.

17. The apparatus of claim 16 wherein:
said tubular fixation element is fastened concentrically on a distal end region of the device.

18. An apparatus for fixation in a body cavity, including:
an elongate bodily insertable device having a proximal end region and a distal end region;
a flexible tubular fixation element and a fastening means for securing a proximal end of the fixation element to a selected region of the device, said fixation element being formable into a delivery configuration in which the fixation element has a delivery diameter, and radially expandable to a fixation configuration in which the fixation element over the majority of its length has a fixation diameter substantially greater than the delivery diameter, said fixation element when in a relaxed state having diameter greater than the fixation diameter; and
a deployment means operatively associated with said device for delivery the fixation element in said delivery configuration as the device is bodily inserted to selectively position the fixation element at a predetermined location within a body cavity, said deployment means including a restraining means for elastically deforming the fixation element into the delivery configuration and maintaining the fixation element in the delivery configuration against a restoring force under which the fixation element tends to radially expand, said restraining means being controllable to allow radial expansion of the fixation element over the majority of its length including a distal end thereof into a surface engagement with a tissue wall segment defining the cavity at said predetermined location, to secure the fixation element to the wall segment and thus substantially fix the selected region within said body cavity.

19. The apparatus of claim 18 wherein:
said tubular fixation element is fastened concentrically on a distal end region of the device.

20. An apparatus for fixation in a body cavity, including:
an elongate bodily insertable device having a proximal end region and a distal end region;
a flexible tubular fixation element and a fastening means for securing a medial portion of the fixation element to a selected region of said device, said fixation element being elastically formable into a deliver configuration in which the fixation element has a delivery diameter, and radially expandable to a fixation configuration in which the fixation element at least over the majority of its length has a fixation diameter substantially greater than the delivery diameter, said fixation element which in a relaxed state having a diameter greater than the fixation diameter; and
a deployment means operatively associated with said device for delivering the fixation element in the delivery configuration as the device is bodily inserted to selectively position the fixation element at a predetermined location within a body cavity, the deployment means including a restraining means for elastically deforming the fixation element into the delivery configuration and maintaining the fixation element in the delivery configuration against a restoring force under which the fixation element tends to radially expand, said restraining means being controllable to allow radial expansion of said fixation element at least along proximal and distal end regions, into a surface engagement with a tissue wall segment defining the cavity at said predetermined location, to secure the fixation element to the tissue wall segment and thus substantially fix the selected region within said body cavity.

21. The apparatus of claim 20 wherein:
said tubular fixation element is fastened along a portion of its circumference to a distal end region of the device, whereby the fixation element when in the fixation configuration, tends to position the distal portion of the device adjacent the tissue wall segment.

* * * * *

UNITED STATES PATENT AND TRADEMARK OFFICE
CERTIFICATE OF CORRECTION

PATENT NO. : 5,071,407
DATED : December 10, 1991
INVENTOR(S) : Termin et al It is certified that error appears in the above-identified patent and that said Letters Patent is hereby corrected as shown below:

Column 11, Claim 18, Line 17, delete "delivery" it should read as -- delivering --.

Column 12, Claim 20, Line 9, delete "deliver" it should read as -- delivery --.

Column 12, Claim 20, Line 14, delete "which" it should read as -- when --.

Signed and Sealed this

First Day of June, 1993

Attest:

MICHAEL K. KIRK

*Attesting Officer*      Acting Commissioner of Patents and Trademarks